United States Patent [19]

Chong

[11] Patent Number: 4,879,111
[45] Date of Patent: Nov. 7, 1989

[54] TREATMENT OF INFECTIONS WITH LYMPHOKINES

[75] Inventor: Kong-Teck Chong, Union City, Calif.

[73] Assignee: Cetus Corporation, Emeryville, Calif.

[21] Appl. No.: 853,122

[22] Filed: Apr. 17, 1986

[51] Int. Cl.$^4$ .................. A61K 45/02; A61K 37/02
[52] U.S. Cl. .................. 424/85.2; 424/85.1; 424/85.5
[58] Field of Search ............ 424/85, 85.1, 85.2, 424/85.4, 85.5

[56] References Cited

U.S. PATENT DOCUMENTS

| | | | |
|---|---|---|---|
| 4,518,584 | 5/1985 | Mark et al. | 424/85 |
| 4,604,377 | 8/1986 | Fernandes et al. | 424/85 |
| 4,650,674 | 3/1987 | Aggarwal et al. | 424/85 |
| 4,677,063 | 6/1987 | Mark et al. | 435/172.3 |

FOREIGN PATENT DOCUMENTS

| | | |
|---|---|---|
| 088540 | 9/1983 | European Pat. Off. |
| 0089062 | 9/1983 | European Pat. Off. |
| 85/04328 | 10/1985 | World Int. Prop. O. |

OTHER PUBLICATIONS

Oeltgen et al., Recent Results Cancer Res, 1980, 75:207–212.
Drews, J., Infection (1985), vol. 13, (Suppl. 2), pp. 241–250 (abstract only).
Goeddel et al., Nature, 287:411–416 (1980).
Williamson et al., *Proc. Natl. Acad. Science*, 80:5397–5401 (1983).
J. Drews, *Infection*, 13, Suppl. 2, pp. 241–250 (1985).
Watson, J. et al., Immunological Rev. (1980) 51:257–278.
Redelman, D. et al., J. Immunol Meth (1983) 56:359–370.
Ruscetti, F. W. et al., Blood (1981) 57:379–393.
Carter, J. et al., Fed Proc (1985) 44:1290.
Stötter, H. et al., Eur J Immunol (1980) 10:719–722.
Reed, S. G. et al., J Immunol (1984) 133:3333.
Farrar, J. J. et al., Immunol Rev (1982) 63:158.
Fong, S. et al., Vet Immunol and Immunopathol (in press).
Stott, J. L. et al., "Human Recombinant INterleukin-2 Augments In Vitro Blastogenesis of Bovine and Procine Lymphocytes" (in press).
Doyle, M. V. et al., Journal of Biological Response Modifiers (1985) 4:96–109.

*Primary Examiner*—Blondel Hazel
*Attorney, Agent, or Firm*—Janet E. Hasak; Gregory J. Giotta; Albert P. Halluin

[57] ABSTRACT

Infections in mammalian hosts may be treated therapeutically or prophylactically with an effective amount of at least one lymphokine before or after host infection, the amount being sufficient to achieve at least 50% protection of the host. Preferably, the lymphokine is IL-2 or a combination of TNF and IL-2 or TNF and IFN-$\gamma$. Also, preferably the infection is bacterial and is being treated prophylactically. The combination of TNF and IL-2 or TNF and IFN-$\gamma$ is administered in synergistically effective amounts.

16 Claims, No Drawings

TREATMENT OF INFECTIONS WITH LYMPHOKINES

BACKGROUND OF THE INVENTION

This invention relates to the use of a lymphokine, alone or in combination with other lymphokines, in the prophylactic or therapeutic treatment of infectious diseases.

It has long been known that microbial infection can be inhibited by a variety of immunomodulating agents. These agents may be classified as: (1) crude immunostimulant of microbial nature (examples are mycobacterium boris strain BCG and the killed vaccine of corynebacterium parvum); and (2) chemically defined immunoadjuvants of bacterial origin (examples are lipopolysaccharides). More recently, various synthetic immunomodulating drugs have been shown to possess antiviral effects. The most promising of these, Inosiplex, has been tested in man and claimed to be effective against a variety of virus infections (Hepatitis A, recurrent Herpes Simplex, Herpes Zoster, influenza-caused common cold). The response, however, has not always been predictable and appears to vary with individual patients.

Lymphokines, such as interleukin-2, interferon-alpha, interferon-gamma, colony stimulating factor, and tumor necrosis factor, are proteins secreted by T cells upon activation by antigens or lectins. Interleukin-2, a lymphokine which is produced by normal peripheral blood lymphocytes and induces proliferation of antigen or mitogen stimulated T cells after exposure to plant lectins, antigens, or other stimuli, was first described by Morgan, D. A., et at., *Science* (1976) 193: 1007–1008. Then called T cell growth factor because of its ability to induce proliferation of stimulated T lymphocytes, it is now recognized that in addition to its growth factor properties it modulates a variety of functions of immune system cells in vitro and in vivo and has been renamed interleukin-2 (IL-2). IL-2 is one of several lymphocyte-produced, messenger-regulatory molecules which mediate immunocyte interactions and functions.

IL-2 was initially made by cultivating human peripheral blood lymphocytes (PBL) or other IL-2-producing cell lines. See, for example, U.S. Pat. No. 4,401,756. Recombinant DNA technology has provided an alternative to PBLs and cell lines for producing IL-2. Taniguchi, T. et al., *Nature* (1983), 302:305–310 and Devos, R., *Nucleic Acids Research* (1983), 11:4307–4323 have reported cloning the human IL-2 gene and expressing it in microorganisms.

U.S. Pat. No. 4,518,584 describes and claims muteins of IL-2 in which the cysteine normally occurring at position 125 of the wild-type or native molecule has been replaced with a neutral amino acid, such as serine or alanine. Copending U.S. application Ser. No. 810,656 filed Dec. 17, 1985 discloses and claims an oxidation-resistant mutein such as IL-2 which is biologically active wherein each methionine residue of the protein from which the mutein is derived which methionine is susceptible to chloramine T or peroxide oxidation is replaced with a conservative amino acid such as alanine. These IL-2 muteins are disclosed as useful in combating bacterial, viral, fungal, parasitic and protozoan infections. U.S. Pat. Nos. 4,530,787 and 4,569,790 disclose and claim methods for purifying recombinant native IL-2 and muteins thereof, as well as the purified form of IL-2.

U.S. Pat. No. 4,604,377 issued Aug. 5, 1986 (PCT WO85/04328) discloses an IL-2 composition suitable for reconstituting in a pharmaceutically acceptable aqueous vehicle composed of oxidized microbially produced recombinant IL-2. The IL-2 is noted as useful in enhancing cell-mediated immune responses in the therapy of viral, parasitic, bacterial, malignant, fungal, protozoal, or mycobacterial or other infectious diseases. In addition, the IL-2 is disclosed as useful for inducing enhanced immunologic response of cells ex vivo in treating infectious diseases, for prophylaxis against infectious diseases and for treating infectious diseases in combination with other lymphokines. The effect of IL-2 on host resistance mechanisms before the onset of specific immune responses has not been studied to applicants' knowledge.

IL-2 is also disclosed as useful as an anti-infective in WO 85/05124 published Nov. 21, 1985 (Sandoz), WO 85/03948 published Sept. 12, 1985 (Celltech), EP 147,819 published July 10, 1985 (Hoffmann-LaRoche), EP 118,617 published Sept. 19, 1984 (Ajinomoto), EP 118,977 published Sept. 19, 1984 (Biogen), Siegel et al., *Infection*, 13,:219–223 (1985), Siegel et al., *Infection*, 12:298–302 (1984, Lane et al., *Cancer Res.*, 45:4674–4676 (1985), Rouse et al., *J. Immunol.*, 134:926–930 (1985, EP 132,754 published Feb. 13, 1985 (Rockefeller University), EP 94,317 published Nov. 16, 1983 (Shionogi), U.S. Pat. Nos. 4,407,945 and 4,473,642 (Immunex), EP 142,268 published May 22, 1985 (Ajinomoto), and EP 89,062 published Sept. 21, 1983 (Ajinomoto). None of these references appear to disclose specific in vivo activity of the IL-2.

Tumor necrosis factor (TNF) was first described by Carswell et al., PNAS (USA) (1975) 72:3666–3670 as an endotoxin-induced serum factor which causes necrosis of chemically transformed tumor cells when growing in mice. Human TNF is known to be cytotoxic to neoplastic cells, and has been produced in recombinant form. See Pennica et al., *Nature* (London) (1984) 312:724–729 and Shirai et al., *Nature* (London) (1985) 313:803–806, Wang et al., *Science* (1985), 228:149–154.

The cloning of rabbit TNF is disclosed in EP No. 146,026, published June 26, 1985 (Dainippon Pharmaceutical Co., Ltd.) and EP No. 148,311, published July 17, 1985 (Asahi Kasei Kogyo Kabushiki). The cloning of human TNF having 151 and 155 amino acids (2 and 6 less than the native form) is disclosed in EP No. 155,549, published Sept. 25, 1985 (Dainippon Pharmaceutical Co., Ltd.), and human TNF having 155 amino acids is disclosed in EP No. 158,286, published Oct. 16, 1985 (Asahi Kasei Kogyo Kabushiki Kaisha) and corresponding GB No. 2,158,829A, published Nov. 20, 1985. The cloning of mature TNF (157 amino acids) and various modified forms (muteins) thereof is disclosed in EP No. 168,214, published Jan. 15, 1986 (Genentech) and PCT No. US85/01921, filed Oct. 3, 1985, published Apr. 1986 (Cetus Corporation). The latter, PCT No. 85/01921 corresponds to U.S Pat. No. 4,677,063 issued June 30, 1987, the disclosure of which is incorporated herein by reference.

Interferons (IFN) constitute a group of naturally occurring proteins which are known to exhibit antiviral, anti-tumor and immunoregulatory behavior. Two types of IFN have been identified based on differences in their observed biological properties and molecular structures: Type I and Type II. Beta-interferon (IFN-$\beta$)

is a Type I IFN which can be induced in fibroblasts by viral challenge and contains about 165 amino acids. IFN-α is also a Type I IFN inducible in leukocytes, and IFN-γ is a Type II IFN which is induced in lymphocytes in response to specific mitogenic stimuli and contains 146 amino acids.

It is known that Type I and Type II interferons (IFN) may be combined to produce a synergistic biological effect. See, for example, Fleishmann, *Cancer Res.* (1982) 42:869–875 (mouse IFNs) and European Patent Publication No. 107,498 published May 2, 1984 (human IFN-γ and IFN-α or β). U.S. Pat. No. 4,518,584 to Mark et al. (Cetus Corporation) discloses the combination of IL-2 muteins with gamma-interferon, B cell growth factor, and IL-1. In addition, it has been disclosed that IL-2 may be used with IFN-γ to treat tumor-bearing hosts with synergistic results (European Patent Publication No. 149,551 published July 24, 1985 (Genentech) and German Patent Publication No. 3411184 published Oct. 31, 1985 (Deut Roten Kreuzes)) or with augmentation of natural killer activity (Svedersky et al., *J. Immunol.* (1984) 133:714–718). Also, Dr. Talmadge of the Preclinical Screening Lab, BRMP has reported in 1986 the augmented effect of using TNF and IFN-γ to treat metastatic disease in mice. EP No. 131,789, published Jan. 23, 1985 (Sloan-Kettering Institute for Cancer Research) and EP No. 168,214, published Jan. 15, 1986 (Genentech) disclose the synergistic effect of TNF and IFN-γ to treat various tumors in mice.

The effect of various lymphokines, alone or in combination, on infectious diseases in vivo has not been extensively studied to date.

SUMMARY OF THE INVENTION

Accordingly, the present invention is directed to a method for prophylactic or therapeutic treatment of infections in mammalian hosts comprising administering an effective amount of a lymphokine from a mammalian species selected from the group consisting of TNF, a mixture of TNF and IL-2, both from a mammalian species, and a mixture of TNF and IFN-γ, both from a mammalian species to the host before or after infection of the host, wherein the amount of lymphokine or mixture is a sufficient dose to achieve at least a 50% protection of the host.

Preferably, the lymphokine is human IL-2 or a combination of human tumor necrosis factor (TNF) and human IL-2 or human interferongamma (IFN-γ). Also in a preferred embodiment the treatment is prophylactic for bacterial infections.

In another aspect, the invention provides a method for prophylactic or therapeutic treatment of infections in mammalian hosts comprising administering at least 100,000 units of IL-2 to the host before or after infection of the host.

In yet another aspect, the invention provides a composition suitable for parenteral administration to mammalian hosts for prophylactic or therapeutic treatment of infections comprising a mixture of TNF and IL-2 or TNF and interferon-γ in synergistically effective amounts.

The combination of IL-2 and TNF in particular provides a surprising synergism in treating infections, where the amount of IL-2 employed is far less than the amount employed if IL-2 is used alone to achieve the same level of survival rate.

DESCRIPTION OF THE PREFERRED EMBODIMENTS

As used herein, the term "recombinant" refers to lymphokines produced by recombinant DNA techniques wherein generally the gene coding for the lymphokine is cloned by known recombinant DNA technology. For example, by using the human lymphokine cDNA as a template, the gene showing complementarity to the human lymphokine cDNA is inserted into a suitable DNA vector such as a bacterial plasmid, preferably an *E. coli* plasmid, to obtain a recombinant plasmid, and the plasmid is used to transform a suitable host. The gene is expressed in the host to produce the recombinant protein. Examples of suitable recombinant plasmids for this purpose include pBR322, pCR1, pMB9 and pSC1. The transformed host may be eucaryotic or procaryotic, preferably a procaryotic host.

As used herein, the term "lymphokine" refers to low molecular weight proteins which are secreted by T cells when antigens or lectins stimulate T cell growth. Examples of lymphokines include, but are not limited to, interferon-alpha, interferon-gamma, interleukin-1 (IL-1), interleukin-2 (IL-2), interleukin-3 (IL-3), tumor necrosis factor (TNF), a colony stimulating factor (e.g. CSF-1, (CSF-G or CSF-GM), chemotaxins, migration inhibitory activity factor (MIF), macrophage-activating factor (MAF), NK cell activating factor, T cell replacing factor, leukocyte-inhibitory factor (LIF), lymphotoxins, osteoclast-activating factor (OAF), soluble immune response suppressor (SIRS), growth-stimulating factor, a monocyte growth factor, etc.

As used herein, the term "pharmaceutically acceptable" refers to a carrier medium which does not interfere with the effectiveness of the biological activity of the active ingredients and which is not toxic to the hosts to which it is administered.

As used herein, the term "prophylactic or therapeutic" treatment refers to administration to the host of the lymphokine(s) either before or after infection. If the lymphokine(s) are administered prior to exposure to the infecting agent, the treatment is prophylactic (i.e., it protects the host against infection), whereas if administered after infection, the treatment is therapeutic (i.e., it combats the existing infection). Preferably, the dose is administered from 18 hours before infection for prophylactic treatment and in early phase of infection for therapeutic treatment, up to 18 hours after infection in later phase of infection for therapeutic treatment.

As used herein, the term "infections" refers to any kind of infectious disease, including those caused by bacteria, fungi, viruses, protozoa or parasites. Examples of bacterial infections include *P. aeruginosa*, *E. coli* tetanus, Mycobacterium species, Streptococcal strains, diphtheria and Salmonella. Examples of fungal infections include cryptococcosis, histoplasmosis, and other infections due to Candida species. Examples of viral infections include Hepatitis A, recurrent Herpes Simplex, AIDS, Herpes Zoster, influenza, and rhinoviruses. Preferably, the infection is bacterial, more preferably Gram-negative infection, and most preferably *P. aeruginosa* and *E. coli* infection.

As used herein, the term "synergistically effective amount" as applied to each lymphokine where more than one are employed refers to the amount of each component of the mixture which is effective in producing more than the additive effect of each component in treating the infection. The difference between additivity and synergism is often difficult to ascertain. Synergy is defined herein in terms of the fractional inhibitory concentration (FIC) index, which is the sum of the FIC's for the individual lymphokines used in each combination, as described by Sande et al., p. 1080-1105 in A. Goodman et al., ed., *The Pharmacological Basis of Therapeutics,* MacMillan Publishing Co., Inc., New York (1980). Under this test, isobolograms may be prepared from the dose response curves for various combinations of the lymphokines. While additive effects generate a straight line as one component is reduced and the other increased, synergistic effects are indicated by a concave curve, where a small increase in the amount of one component will compensate for a large decrease in the amount of the other component.

The method of this invention involves administering to a mammalian host, preferably a human host, an effective amount of one or more lymphokines. If more than one lymphokine is employed, they may be combined in vitro before administration or separately administered to the host, in either order or simultaneously, with any second administration taking place generally within about 10 minutes of the first administration.

The administration(s) may take place by any suitable technique, including subcutaneous and parenteral administration, preferably parenteral. Examples of parenteral administration include intravenous, intraarterial, intramuscular, and intraperitoneal, with intravenous being preferred.

The dose and dosage regimen will depend mainly on whether the lymphokine(s) is/are being administered for therapeutic or prophylactic purposes, separately or as a mixture, the type of infection, the patient, the patient's history, the type of lymphokine, and whether more than one type of lymphokine is being employed. The amount must be effective to achieve a protection level of at least 50%, preferably at least 70%; dosages which do not achieve this minimal level of effectiveness may not be employed. The doses may be single doses or multiple doses over a period of several days, but single doses are preferred. For purposes herein, a protection level of at least 50% means that at least 50% of the treated hosts exhibit improvement against the infection, including but not limited to improved survival rate, more rapid recovery, or improvement or elimination of symptoms.

If IL-2 is employed alone, the dosage level is generally at least 100,000 units, more preferably 100,000-250,000 units, and most preferably at least 200,000 units up to a maximally tolerated dose, i.e., one which is not toxic to the host, as measured by adverse side effects of death. If IL-2 is employed with TNF, the preferred range for optimum synergy is 15,000-30,000 units of IL-2 and 0.01-0.02 $\mu$g of TNF per dose. If TNF is employed with IFN-$\gamma$, the preferred range for optimum synergy is 100 units of IFN-$\gamma$ and 0.1 $\mu$g of TNF per dose.

For parenteral administration the lymphokine(s) will generally be formulated in a unit dosage injectable form (solution, suspension, emulsion), preferably in a pharmaceutically acceptable carrier medium which is inherently non-toxic and non-therapeutic or non-prophylactic. Examples of such vehicles include saline, Ringer's solution, dextrose solution, mannitol, and normal serum albumin. Nonaqueous vehicles such as fixed oils and ethyl oleate may also be used. The carrier medium may contain minor amounts of additives such as substances which enhance isotonicity and chemical stability, e.g., buffers and preservatives. The lymphokine(s) will typically be formulated in such carriers at a concentration of about 0.1 mg/ml to 100 mg/ml of each, preferably 0.2 to 1 mg/ml of each.

Alternatively, if the lymphokine is IL-2, it may be made into a sterile, stable lyophilized formulation in which the purified IL-2 is admixed with a water-soluble carrier such as mannitol, which provides bulk, and a sufficient amount of sodium dodecyl sulfate to ensure the solubility of the recombinant IL-2 in water. The formulation is suitable for reconstitution in aqueous injections for parenteral administration and it is stable and well-tolerated in human patients. The formulation method is more completely described in PCT No. WO 85/04328, the disclosure of which is incorporated herein by reference.

As mentioned above, the lymphokine employed herein may be any lymphokine, obtained from tissue cultures or by recombinant techniques, and from any mammalian source such as, e.g., mouse, rat, rabbit, primate, pig, and human. Preferably the lymphokine is derived from a human source and more preferably is a human recombinant lymphokine. Most preferably the lymphokine is recombinant human interleukin-2 alone or in combination with recombinant human TNF or human IFN-$\gamma$. The recombinant IL-2 may be obtained as described by Taniguchi et al., *Nature,* 302:305-310 (1983) and Devos, *Nucleic Acids Research,* 11:4307-4323 (1983) by cloning the native human IL-2 gene and expressing it in transformed microorganisms. It may also be an IL-2 mutein as described in U.S. Pat. No. 4,518,584, in which the cysteine normally occurring at position 125 of the wild-type or native molecule has been replaced by a neutral amino acid such as serine or alanine, or an IL-2 mutein as described in copending U.S. application Ser. No. 810,656 filed Dec. 17, 1985, the disclosure of which is incorporated herein by reference, in which the methionine normally occurring at position 104 of the wild-type or native molecule has been replaced by a neutral amino acid such as alanine.

Preferably, the IL-2 is an unglycosylated protein which is produced by a microorganism which has been transformed with the human cDNA sequence or a modified human cDNA sequence of IL-2 which encodes a protein with an amino acid sequence at least substantially identical to the amino acid sequence of native human IL-2, including the disulfide bond of the cysteines at positions 58 and 105, and has biological activity which is common to native human IL-2. Substantial identity of amino acid sequences means the sequences are identical or differ by one or more amino acid alterations (deletions, additions, substitutions) which do not cause an adverse functional dissimilarity between the synthetic protein and native human IL-2. Examples of IL-2 proteins with such properties include those described by Taniguchi et al., *Nature* (1983), 301:305-310; Devos, *Nucleic Acids Research* (1983), 11:4307-4323; and by European Patent Publication Nos. 91,539 and 88,195; in U.S. Pat. No. 4,518,584, supra, and in copending U.S. application Ser. No. 810,656 filed Dec. 17, 1985, supra. Most preferably, the IL-2 is the des-ala$_1$-IL-2$_{ser125}$ mutein in which the initial terminal alanine is deleted and the cysteine at position 125 is replaced by a serine residue.

The IL-2 may be produced and purified to clinical purity by the method described and claimed in U.S. Pat. No. 4,569,790, issued Feb. 11, 1986, the disclosure of which is incorporated herein by reference.

The recombinant human TNF may be obtained as described by Pennica et al., *Nature,* 312:724–729 (1984); Yamada et al., *J. Biotechnology,* (1985) 3:141–153; Wang et al., *Science* (1985), 228:149–154; EP No. 155,549 published Sept. 29, 1985, EP No. 158,286 published Oct. 16, 1985; EP No. 168,214 published Jan. 15, 1986; and PCT No. US85/01921 published April, 1986. The recombinant rabbit TNF may be obtained as described in EP No. 146,026 published June 26, 1985 and EP No. 148,311 published July 17, 1985. Preferably the TNF is a human TNF mutein wherein the first eight amino acid residues have been deleted, using the procedure described in U.S. Pat. No. 4,677,063 issued June 30, 1987 or the TNF is a cysteine-depleted mutein described in copending U.S. Ser. No. 698,939 filed Feb. 7, 1985 and in U.S. Pat. No. 4,518,584, supra.

Recombinant human IFN-γ may be obtained as described by Gray et al., *Nature,* 295:503 (1982).

The various aspects of the invention are further described by the following examples, which are not intended to limit the invention in any manner. For example, the test used in the examples for % protection is % survival rate, which is only one test of many which may be employed to determine the extent of protection in the host. In these examples all parts for solids are by weight and all percentages for liquids and gases are by volume, unless otherwise noted, and all temperatures are given in degrees Celsius.

EXAMPLE 1

Use of IL-2 to treat Gram-negative Infections
A. General Treatment
Mice

Female CD1 mice (Charles River Laboratories, Inc., Wilmington, Mass.) and male CBA/NJ and C57BL/6J-bg (beige) mice (Jackson Laboratories, Bar Harbor, Me.) which were all 6–8 weeks old were employed in the in vivo tests.

IL-2

The recombinant IL-2 employed in this example was des-ala IL-$2_{ser125}$. The amino acid sequence of this IL-2 differs from the amino acid sequence of native human IL-2 in that it lacks the initial alanine of the native molecule, and the cysteine at position 125 has been changed to serine. Samples of *E. coli* that produce this IL-2 have been deposited by Cetus Corporation in the American Type Culture Collection, 12301 Parklawn Drive, Rockville, Md., USA on Sept. 26, 1983 under accession number 39,452 and on Mar. 6, 1984 under accession number 39,626 under the provisions of the Budapest Treaty.

The IL-2 was processed and purified as described in the text and FIG. 1 of U.S. Pat. No. issued Aug. 5, 1986 the disclosure of which is incorporated herein by reference, except that the oxidation was carried out using copper chloride, as described in U.S. Pat. No. 4,572,798 rather than o-iodosobenzoate. When the IL-2 was recovered from the chromatography step(s) it was lyophilized and resuspended in a neutral aqueous buffer containing the reducing agent (DTT) to keep the IL-2 in a reduced state and a solubilizing agent to keep it in solution. The purity of the recombinant IL-2 after the chromatography step(s) was at least about 95% and the IL-2 contained less than about 0.02 ng/ml endotoxin as determined by the Limulus amebocyte assay.

The purified IL-2 was formulated at a concentration of 0.3 mg/ml with 50 mg/ml mannitol.

Bacteria

*E. coli* SM18, a type 02 clinical isolate from a bacteremic patient at Sait Mary's Hospital, San Francisco, Calif., was cultured overnight in brain-heart infusion broth (Difco Laboratories, Detroit, Mich.) at 37°C., harvested by centrifuging at 6000 rpm for 15 minutes, washed in standard phosphate buffered saline (PBS) resuspended in brain-heart infusion broth containing 20% glycerol, aliquoted, and stored at −70° C. The viability of the bacteria was determined by plating tenfold serial dilutions onto starch agar plates and counting the colony-forming units (cfu) after a 24-hour incubation at 37° C. The titre was expressed as the mean number of cfu/ml of stock bacteria. The bacteria were prepared for injection by diluting a freshly thawed vial in PBS at room temperature.

Another clinical isolate, *Pseudomonas aeruginosa* (from Dr. Lowell Young, UCLA, Los Angeles, Calif.) was cultured, harvested, washed, evaluated and prepared for injection as described above.

Injections

The test animals were randomly distributed into groups of 10 or 12. IL-2 or saline or excipient buffer consisting of 50 μg/ml sodium dodecyl sulfate (SDS), 5% by volume mannitol and 10mM mono-and di-basic sodium phosphate at pH 7.5 was administered intraperitoneally in a single dose to the mice 18 hours before intraperitoneal injection with 0.5 ml of a serial ten-fold dilution of viable bacteria in sterile saline. The bacteria were administered at 1 × minimal $LD_{100}$, where $LD_{100}$ represented the minimum number of bacteria necessary to kill all the mice within a group.

The mice were observed daily and mortality was recorded for 4 to 7 days.

The statistical significance of the % survival numbers, indicated in the tables below by parentheses, was computed using the standard one-tailed Fisher Exact test for all experiments. This test is described by W. J. Conover, *Practical Nonparametric Statistics* (J. Wiley and Sons:New York, 1980).

B. Specific Experiments

1. Groups of ten or 12 CD1 mice were treated with 200,000 units per mouse IL-2 or excipient buffer, intraperitoneally, 18 hours prior to infection with the $LD_{100}$ (6 × $10^7$ cfu) of *E. coli* SM18 per mouse intraperitoneally. The test dose of both IL-2 and excipient contained less than 0.002 ng endotoxin per mouse. The results are shown in Table I, after 7 days.

TABLE I

| Exp. | No. Mice/Group | Treatment | % Survival |
|---|---|---|---|
| 1 | 10 | IL-2 | 80 (p < 0.01) |
|   | 10 | Saline | 0 |
| 2 | 12 | IL-2 | 90 (p < 0.001) |
|   | 12 | Excipient | 0 |
| 3 | 10 | IL-2 | 90 (p < 0.005) |
|   | 10 | Excipient | 0 |

2. Groups of ten CD1 mice were treated with 200,000 units per mouse IL-2 or saline, intraperitoneally, 18 hours prior to infection with an $LD_{100}$ dose (which varies with bacteria) of one of two bacteria, intraperitoneally. The results are shown in Table II, after seven days.

TABLE II

| Infection | Treatment | % Survival |
|---|---|---|
| *E. coli* SM18 ($LD_{100}$ = 6.0 × $10^7$ cfu/mouse) | IL-2 | 83 (p = 0.008) |
|  | Saline | 0 |

TABLE II-continued

| Infection | Treatment | % Survival |
|---|---|---|
| P. aeruginosa (LD$_{100}$ = 6.0 × 10$^7$ cfu/mouse) | IL-2 Saline | 83 (p = 0.008) 0 |

3. Groups of ten CD1 mice were treated with 200,000 units/mouse, 100,000 units/mouse, 50,000 units/mouse, or 10,000 units/mouse of IL-2 intraperitoneally 18 hours prior to infection with an LD$_{100}$ (6×10$^7$ cfu/mouse) of E. coli SM18. Saline control animals were treated with IL-2 intraperitoneally 18 hours prior to an injection of saline intraperitoneally. Table III shows percent of mice surviving as a function of hours, up to 168 hours (7 days) post-infection.

TABLE III

| Treatment | % Survival at various Times Post-Infection (hours) | | | | | | | |
|---|---|---|---|---|---|---|---|---|
| | 0 | 24 | 48 | 72 | 96 | 120 | 144 | 168 |
| IL-2 (200,000 U) | 100 | 90 | 80 | 80 | 80 | 80 | 80 | 80 |
| IL-2 (100,000 U) | 100 | 60 | 50 | 50 | 50 | 50 | 50 | 50 |
| IL-2 (50,000 U) | 100 | 70 | 40 | 40 | 40 | 40 | 40 | 40 |
| IL-2 (10,000 U) | 100 | 40 | 30 | 30 | 30 | 30 | 30 | 30 |
| Saline noninfected control | 100 | 100 | 100 | 100 | 100 | 100 | 100 | 100 |
| Excipient control | 100 | 20 | 0 | 0 | 0 | 0 | 0 | 0 |

4. Groups of ten CD1 mice were treated with 200,000 units/mouse of IL-2 intraperitoneally at various times prior or subsequent to an infection with an LD$_{100}$ dose (6×10$^7$ cfu/mouse) of E. coli SM18 intraperitoneally. Table IV shows the percent of mice surviving on day 7 post-infection.

TABLE IV

| Timing of Treatment Hours before (−) or after (+) infection | % Survival |
|---|---|
| −72 | 1 |
| −48 | 1 |
| −24 | 30 |
| −18 | 80 |
| −4 | 80 |
| −2 | 80 |
| −1 | 80 |
| 0 | 1 |
| 1 | 1 |
| 4 | 1 |

5. Groups of ten CD1 mice were treated with 200,000 units/mouse of IL-2 or saline 18 hours before infection with an LD$_{100}$ dose (6×10$^7$ cfu/mouse for intraperitoneal (ip) injection and 2×10$^8$ cfu/mouse for intravenous (iv) injection) of bacteria. Table V indicates the results of varying the routes of administration.

TABLE V

| Bacterial Route | Treatment | Treatment Route | % Survival |
|---|---|---|---|
| ip | IL-2 | ip | 90 (p < 0.002) |
| | Saline | ip | 0 |
| iv | IL-2 | iv | 67 (p = 0.03) |
| | Saline | iv | 0 |
| ip | IL-2 | iv | 0 |
| | Saline | iv | 0 |
| iv | IL-2 | ip | 0 |
| | Saline | ip | 0 |

6. Groups of ten immunodeficient beige or CBA/NJ mice were treated intraperitoneally with 200,000 units/mouse of IL-2 or excipient buffer 18 hours before infection intraperitoneally with an LD$_{100}$ dose (6×10$^7$ cfu/mouse) of bacteria. Table VI shows the percent of mice surviving on day 7 post-infection.

TABLE VI

| Mouse Strain | Immune Defect | Treatment | % Survival |
|---|---|---|---|
| Beige mice | Low NK activity | IL-2 | 100 (p < 0.001) |
| | | Excipient | 0 |
| CBA/NJ mice | B-cell deficiency | IL-2 | 42 |
| | | Excipient | 0 |

7. Groups of ten CD1 mice were treated intraperitoneally with 200,000 units/mouse of IL-2 two hours prior to infection with an LD$_{100}$ dose (6×10$^7$ cfu/mouse or 6×10$^6$ cfu/mouse when carrageenan (Sigma, type IV) was also injected) of E. coli SM18. In groups 2 and 3, mice were also injected intraperitoneally with carrageenan at 1 mg/mouse 30 minutes prior (−30) or subsequent (+30) to IL-2 administration. The survival results after 7 days are given in Table VII, where +− means presence and − means absence.

TABLE VII

| Mice Group | Carragenon | IL-2 (-2 hr) | % Survival |
|---|---|---|---|
| 1 | + | − | 10 |
| 2 | + (−30 min) | + | 0 |
| 3 | + (+30 min) | + | 10 |
| 4 | − | + | 100 |

C. Conclusions

The results of this example show that prophylactic administration of IL-2 protected mice from a lethal Gram-negative bacterial infection. The protection observed was immunologically nonspecific (observed with two clinical isolates of E. coli and a Pseudomonas aeruginosa isolate). The effect was dose dependent, with 100,000 units giving 50% survival rate. The protective effect was fully inducible as early as one hour and up to 18 hours following IL-2 administration.

In addition, the protective effect was route-dependent. Also, IL-2 was effective in NK-deficient mice as well as in the outbred CD1 mice, but was less effective in B-cell deficient mice. Carrageenan, a high molecular weight polygalactose which impairs macrophage function, abolished the IL-2 effect, indicating that the effect may be mediated through phagocyte activation.

EXAMPLE 2

Use of IL-2 and TNF to Treat Gram-Negative Infections TNF

A mutein of human TNF having the first eight amino acids deleted from the N-terminus was prepared as described in copending U.S. Ser. No. 760,661 filed July 30, 1985, the disclosure of which is incorporated herein by reference. Briefly, TNF was induced from HL-60 cells and purified and sequenced. Then an intronless sequence encoding human TNF was prepared by producing enriched mRNA, constructing a cDNA library, selecting a probe and probing the library to recover the sequence. Then an ATG start codon was introduced immediately preceding the GTC sequence encoding N-terminal valine of the mature protein by site-directed mutagenesis. Clones were selected and strands ligated into expression vectors to obtain procaryotic expression of the mutein. The mutein was then suspended in a formulation buffer.

Experiment

Female CD1 mice (Charles River Laboratories, Inc., Wilmington, Mass.), randomly distributed into groups of 15, were injected intraperitoneally in a single dose with either saline, 0.01 µg per dose of recombinant TNF described above, 10,000 units per dose of recombinant IL-2 described in Example 1, or 0.01 µg of the TNF followed immediately by 10,000 units of the IL-2. Four hours after this injection the mice were injected intraperitoneally with the $LD_{100}$ ($6 \times 10^7$ cfu) of $E.\ coli$ SM18 per mouse. The results in Table VIII show mortality rates after seven days.

TABLE VIII

| Treatment | % Survival |
| --- | --- |
| TNF | 17 |
| IL-2 | 17 |
| TNF and IL-2 | 76 ($p < 0.01$) |
| Saline | 0 |

The results show that the combination of IL-2 and TNF has a synergistic rather than additive effect on combating bacterial infections.

EXAMPLE 3

Use of TNF and IFN-γ to Treat Gram-Negative Infections

Female CD1 mice (Charles River Laboratories, Inc., Wilmington, Mass.) were injected intraperitoneally in a single dose with either saline, 0.1 µg per dose of recombinant TNF described in Example 2, 100 units per dose of IFN-γ (Cellular Products Inc.), or a mixture prepared in vitro of 0.1 µg per dose of the TNF and 100 units per dose of the IFN-µ. Four hours after this injection the mice were injected intraperitoneally with the $LD_{100}$ ($6 \times 10^7$ cfu) of $E.\ Coli$ SM18 per mouse. The results in Table IX show mortality rates after seven days.

TABLE IX

| Treatment | % Survival |
| --- | --- |
| TNF | 50 |
| IFN-γ | 20 |
| TNF and IFN-γ | 80 ($p < 0.01$) |
| Saline | 0 |

The results show that TNF and IFN-γ can be combined to give an additive/synergistic effect on combating bacterial infection.

In summary, the present invention is seen to provide an effective therapeutic and prophylactic composition to combat infections which contains one or more lymphokines, preferably IL-2. The combination of IL-2 and TNF results in synergy.

Modifications of the above-described modes for carrying out the invention which are obvious to those skilled in the fields of molecular and clinical biology, pharmacology, and related fields are intended to be within the scope of the following claims.

What is claimed is:

1. A method for prophylactic or therapeutic treatment of bacterial infections in mammalian hosts comprising administering an effective amount of tumor necrosis factor (TNF) from a mammalian species, to the host, before or after infection of the host, wherein the amount of TNF is a sufficient dose to achieve at least 50% protection of the host.

2. The method of claim 1 wherein the TNF is from a human source.

3. The method of claim 2 wherein the TNF is recombinant and the treatment is prophylactic.

4. The method of claim 3 wherein the TNF is microbially produced.

5. The method of claim 4 wherein the TNF has its first eight amino acid residues deleted.

6. The method of claim 1 wherein the amount of TNF is a sufficient dose to achieve at least 70% protection of the host.

7. The method of claim 1 wherein the bacterial infection is a Gram-negative infection.

8. The method of claim 1 wherein the TNF is in admixture with a pharmaceutically acceptable carrier medium prior to administration.

9. A method for prophylactic or therapeutic treatment of bacterial infections in mammalian hosts comprising administering an effective amount of tumor necrosis factor (TNF) and interleukin-2 (IL-2), both from a mammalian species, to the host, before or after infection of the host, wherein the amount of TNF and IL-2 is a sufficient dose to achieve at least 50% protection of the host.

10. The method of claim 9 wherein the IL-2 and TNF are from a human source, the amount of IL-2 employed is 15,000-30,000 units and the amount of TNF employed is 0.01-0.02 micrograms per ml.

11. A method for propylactic or therapeutic treatment of bacterial infections in mammalian hosts comprising administering an effective amount of tumor necrosis factor (TNF) and interferon-gamma (IFN-γ), both from a mammalian species, to the host, before or after infection of the host, wherein the amount of TNF and IFN-γ is a sufficient dose to achieve at least 50% protection of the host.

12. The method of claim 11 wherein the TNF and IFN-γ are from a human source.

13. A method for prophylactic or therapeutic treatment of bacterial infections in human host comprising administering an effective amount of recombinant microbial produced human TNF to said host before or after the infection, wherein said amount of TNF is a sufficient dose to achieve at least 50% protection of said host.

14. A method for prophylactic or therapeutic treatment of gram negative bacterial infections in human host comprising administering an effective amount of recombinant microbial produced human TNF to said host before or after the infection, wherein said amount of TNF is a sufficient dose to achieve at least 50% protection of said host.

15. The method of claim 13, wherein said TNF is a mutein of TNF that lacks the first eight amino acids at the amino terminal end.

16. The method of claim 14, wherein said TNF is a mutein of TNF that lacks the first eight amino acids at the amino terminal end.

* * * * *